United States Patent
Jonsson et al.

(10) Patent No.: US 9,925,072 B2
(45) Date of Patent: Mar. 27, 2018

(54) PROSTHETIC SYSTEM FOR REMOVING FLUID OR SWEAT FROM INSIDE OF A LINER WITH FIRST AND SECOND INDEPENDENTLY SEALED VOLUMES

(71) Applicant: Ossur Iceland ehf, Reykjavik (IS)

(72) Inventors: Grimur Jonsson, Reykjavik (IS); Andrew Bache, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

(21) Appl. No.: 15/246,661

(22) Filed: Aug. 25, 2016

(65) Prior Publication Data

US 2017/0056212 A1 Mar. 2, 2017

Related U.S. Application Data

(60) Provisional application No. 62/209,421, filed on Aug. 25, 2015.

(51) Int. Cl.
*A61F 2/80* (2006.01)
*A61F 2/78* (2006.01)
(Continued)

(52) U.S. Cl.
CPC .............. *A61F 2/80* (2013.01); *A61F 2/7812* (2013.01); *A61F 7/00* (2013.01);
(Continued)

(58) Field of Classification Search
CPC .. A61F 2/78; A61F 2/7812; A61F 2/80; A61F 2002/7818; A61F 2002/7868; A61F 2002/802–2002/807; A61F 2007/0051
See application file for complete search history.

(56) References Cited

U.S. PATENT DOCUMENTS 708,685 A * 9/1902 White .................... A61F 2/602
623/26
4,655,779 A * 4/1987 Janowiak .............. A61F 2/7843
623/37
(Continued)

FOREIGN PATENT DOCUMENTS

DE 102010020262 A1 11/2011
EP 0363654 A2 * 4/1990 .............. A61F 2/80
(Continued)

OTHER PUBLICATIONS

International Search Report from PCT Application No. PCT/US2016/048532, dated Oct. 26, 2016.
(Continued)

*Primary Examiner* — Marcia Watkins
(74) *Attorney, Agent, or Firm* — Workman Nydegger

(57) ABSTRACT

A prosthetic system includes a liner adapted to receive a residual limb and having a liner body formed from an elastomeric material. The liner body defines an outer surface and an inner surface opposite the outer surface. The inner surface includes a first part arranged to form a seal between the liner and the residual limb, and a second part of the inner surface has at least one flow channel arranged for promoting movement of fluid away from a skin surface of the residual limb. An outlet is defined in the second part and extends between the inner and outer surfaces. The at least one flow channel is defined in the elastomeric material forming the liner body and is in fluid communication with the outlet.

14 Claims, 5 Drawing Sheets

(51) Int. Cl.
    *A61F 7/00*    (2006.01)
    *A61F 2/76*    (2006.01)
    *A61F 2/50*    (2006.01)

(52) U.S. Cl.
    CPC ............... *A61F 2002/5007* (2013.01); *A61F 2002/7655* (2013.01); *A61F 2002/802* (2013.01); *A61F 2002/805* (2013.01); *A61F 2002/807* (2013.01); *A61F 2007/0051* (2013.01)

(56) References Cited

U.S. PATENT DOCUMENTS

| | | |
|---|---|---|
| 4,869,250 A | 9/1989 | Bitterly |
| 5,885,509 A | 3/1999 | Kristinsson |
| 6,010,528 A | 1/2000 | Augustine et al. |
| 6,136,039 A | 10/2000 | Kristinsson et al. |
| 6,485,776 B2 | 11/2002 | Janusson et al. |
| 6,626,852 B2 | 9/2003 | Janusson et al. |
| 6,706,364 B2 | 3/2004 | Janusson et al. |
| 7,001,563 B2 | 2/2006 | Janusson et al. |
| 7,105,122 B2 | 9/2006 | Karason |
| 7,118,602 B2 | 10/2006 | Bjarnason |
| 8,052,760 B2 | 11/2011 | Egilsson et al. |
| 8,097,043 B2 | 1/2012 | Egilsson |
| 8,182,547 B2 | 5/2012 | King |
| 8,308,817 B2 | 11/2012 | Egilsson et al. |
| 8,475,537 B2 | 7/2013 | King |
| 8,480,759 B2 | 7/2013 | Pacanowsky et al. |
| 9,155,636 B1 * | 10/2015 | Fikes .................... A61F 2/7812 |
| 2001/0016781 A1 | 8/2001 | Caspers |
| 2003/0109908 A1 | 6/2003 | Lachenbruch et al. |
| 2004/0122528 A1 * | 6/2004 | Egilsson ............... A61F 2/7812 623/34 |
| 2005/0149202 A1 | 7/2005 | Schaffer et al. |
| 2007/0055383 A1 | 3/2007 | King |
| 2007/0213839 A1 | 9/2007 | Nachbar |
| 2010/0125342 A1 | 5/2010 | King |
| 2010/0185300 A1 | 7/2010 | Mackenzie |
| 2010/0274364 A1 | 10/2010 | Pacanowsky et al. |
| 2010/0312360 A1 | 12/2010 | Caspers |
| 2011/0071649 A1 | 3/2011 | McKinney |
| 2011/0144769 A1 | 6/2011 | Nakamura |
| 2011/0282466 A1 | 11/2011 | Laghi |
| 2012/0191217 A1 * | 7/2012 | Mackenzie ............... A61F 2/80 623/34 |
| 2013/0025315 A1 | 1/2013 | Freeman et al. |
| 2013/0103125 A1 | 4/2013 | Radspieler et al. |
| 2014/0025183 A1 | 1/2014 | Kelley et al. |
| 2014/0379097 A1 | 12/2014 | Hurley et al. |

FOREIGN PATENT DOCUMENTS

| | | |
|---|---|---|
| EP | 1875881 A1 | 1/2008 |
| WO | 2014182767 A1 | 11/2014 |

OTHER PUBLICATIONS

International Search Report from International Application No. PCT/US2015/011026, dated May 8, 2015.
Ossur, "Icecross Seal-In X5: For TF/TF Users, Instructions for Use", www.ossur.com, 2010, 68 Pages.
"Prototype Prosthetic Cooling System Wins UTSA Entrepreneurship Competition", OandP.com, May 3, 2013, 3 Pages. Retrieved from Internet on Apr. 20, 2016, http://www.oandp.com/articles/news_2013-05-03_02.asp.

* cited by examiner

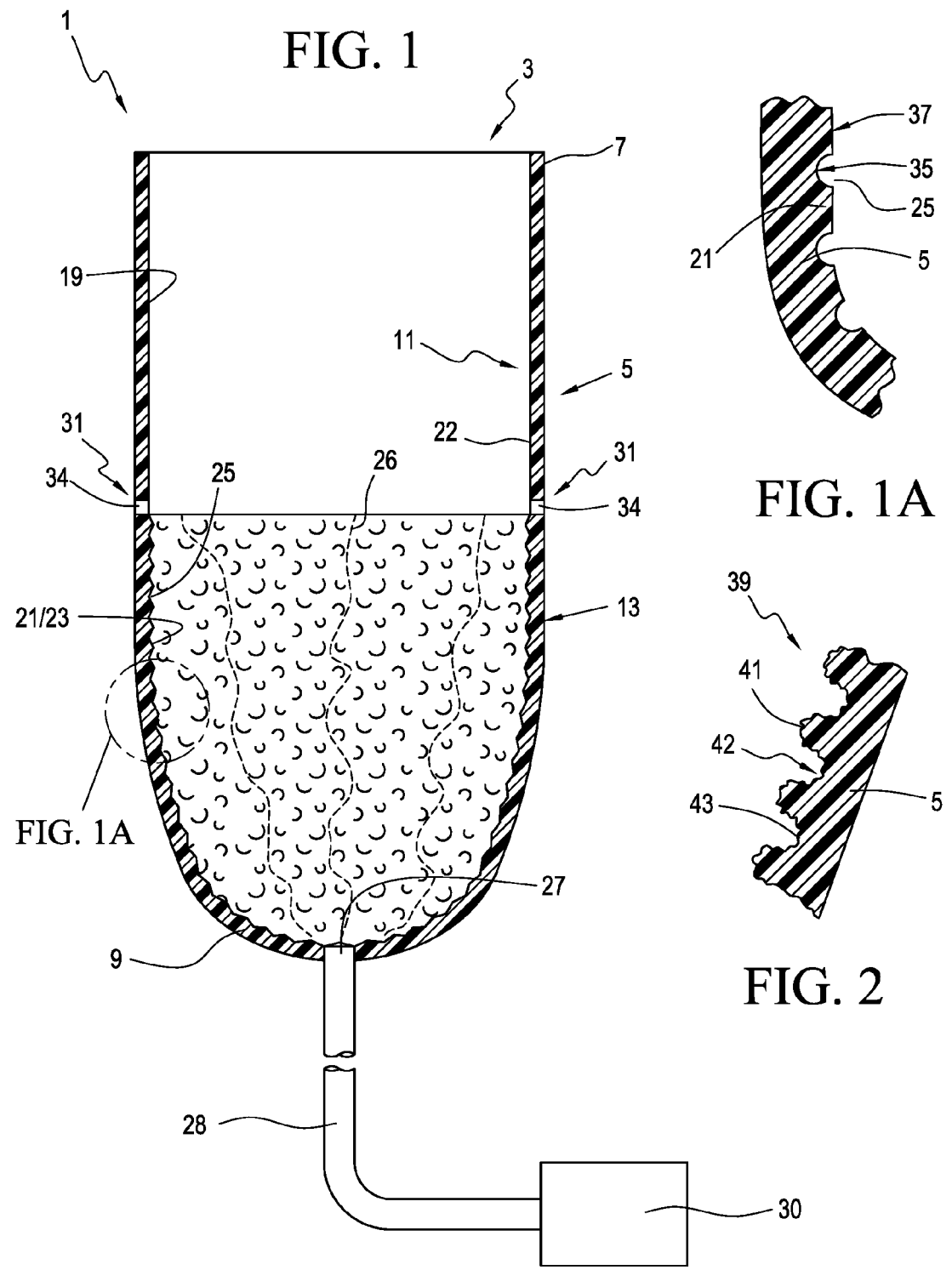

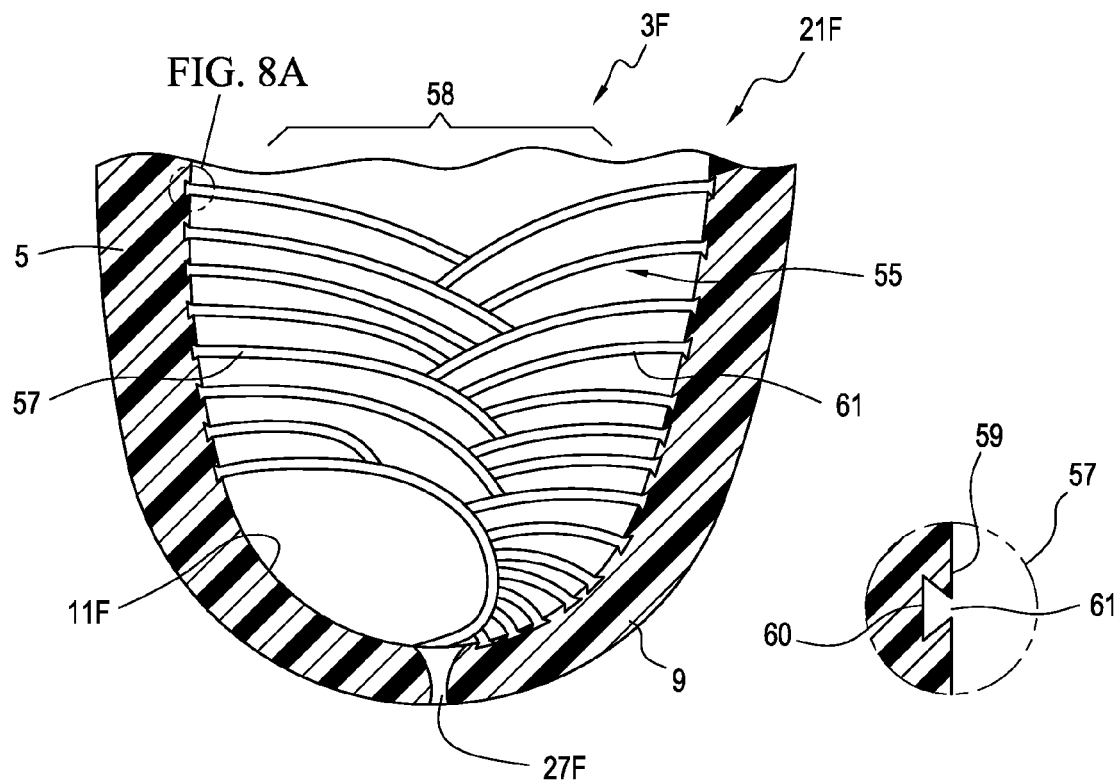
FIG. 8
FIG. 8A
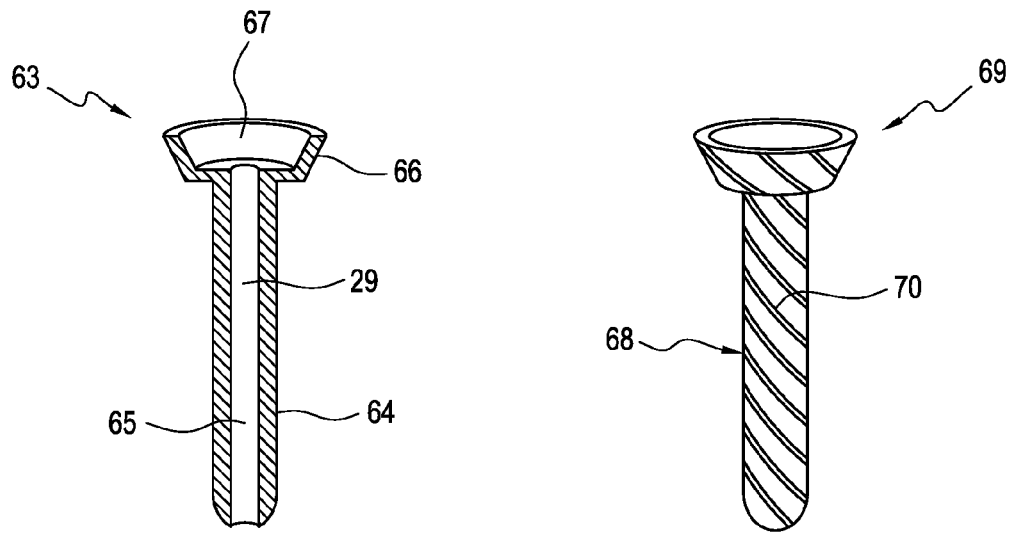
FIG. 10
FIG. 11

PROSTHETIC SYSTEM FOR REMOVING FLUID OR SWEAT FROM INSIDE OF A LINER WITH FIRST AND SECOND INDEPENDENTLY SEALED VOLUMES

TECHNICAL FIELD

The disclosure relates to a prosthetic socket system for fluid or sweat management inside of a liner.

BACKGROUND

Prosthetic liners made of solid elastomer like silicone, copolymer gel, or polyurethane have been commercially available and used for a number of years as the media next to the skin in the majority of lower extremity prostheses.

Such liners have solved many issues like friction and pressure distribution; however, it has been difficult to achieve effective heat and sweat management when using a non-porous interface. For instance, moisture (e.g. sweat or condensation) within the liner can adversely affect limb health. Moisture decreases the friction suspending the liner on the residual limb. This can cause a pistoning action, which describes the relative movement between the liner and the residual limb.

Excessive limb pistoning tends to lead to friction-related injuries such as friction blisters and skin irritation. It also creates the potential for catastrophic failure of the suspension of the limb. Problems such as dermatitis and infection are also common, particularly if the liner and residual limb are not cleaned appropriately or frequently.

Attempts have been made to more effectively remove heat and sweat from liners using different liner type suction interfaces, yet, such interfaces are relatively complex, short lasting, ineffective, uncomfortable, and inevitably prohibit their use with a large majority of users. For instance, one approach includes venting a locking liner by letting air approximately half way up its length and pumping out air distally, with a wicking sock passing the air over the limb. This approach however is rather bulky, complex, and ineffective.

Another approach applies an elevated vacuum to draw sweat across the proximal edge of a prosthetic liner. Sweat however tends to accumulate at the bottom of a liner and elevated vacuum does not reverse that. Further, this elevated vacuum tends to seal in the inside of the liner and the proximal edge, preventing removal of the sweat. In addition, elevated vacuum applied to the proximal edge of the liner tends to cause blisters, making the liner extremely uncomfortable.

Another approach is to cool down the liner, for example, with a tempering buffer in the form of phase change material embedded in the liner body, reducing sweating to a less than desirable degree since the body cannot cool off without perspiration.

There is thus a need for a prosthetic system that provides simple, comfortable, and effective heat and moisture management.

SUMMARY

Embodiments of the prosthetic system provide heat and moisture management by providing a liner with an inner surface arranged to both form a seal between the liner and a residual limb inserted in the liner and promote movement of fluid away from a skin surface of the residual limb. For instance, the inner surface can define a first or proximal part arranged for forming a seal between the proximal part and the residual limb. Below the proximal part, the inner surface can include a second or distal part defining flow channels or spaces in the material forming the liner. When the liner is donned on a residual limb, the spaces or flow channels provide areas of lower pressure into which fluid can flow between the distal part and the skin surface. In the event the residual limb begins to sweat, at least some of the sweat can flow away from the skin surface and collect in the spaces or flow channels, providing a wicking or moisture removal effect.

Because the proximal part of the inner surface seals against the user's skin surface, the spaces or flow channels can be present on the distal part without compromising the fit of the liner on the residual limb. This advantageously allows the prosthetic system to both positively secure the residual limb within the liner and promote movement of fluid away from the skin surface, increasing user comfort and safety.

The spaces or flow channels along the inner surface of the liner itself thus beneficially provide a solution which effectively extracts fluid from the surface of the skin. Conventional methods to obtain wicking/removal of fluid have nearly always, if not solely, relied on some kind of fabric to wick and contain moisture. As noted above, the flow channels or spaces can be defined in the material forming the liner. This advantageously results in a liner which is much easier to maintain, clean, and use than a multicomponent, fabric based system as in the prior art where hygiene is always an issue.

According to an embodiment, the prosthetic system includes a liner adapted to receive a residual limb and having a liner body formed from an elastomeric material. The liner body defines an outer surface and an inner surface opposite the outer surface. The inner surface includes a first part arranged to form a seal between the liner and the residual limb, and a second part of the inner surface has at least one flow channel arranged for promoting movement of fluid away from a skin surface of the residual limb. An outlet is defined in the second part and extends between the inner and outer surfaces. The at least one flow channel is defined in the elastomeric material forming the liner body and is in fluid communication with the outlet.

Fluid or sweat generated at the interface between the second part and the skin surface can move into the at least one flow channel, extracting the fluid or sweat away from the skin surface. Once in the flow channel, the fluid or sweat can be drained or drawn through the at least one flow channel toward the outlet of the liner. According to a variation, the fluid or sweat can be actively drawn through the at least one flow channel toward the outlet using a pump system.

According to a variation, the prosthetic system includes a socket having an interior surface defining a socket cavity. A first sealed volume is defined between a first portion of the outer surface of the liner and a corresponding portion of the interior surface of the socket. A second sealed volume is defined between a second portion of the outer surface of the liner and a corresponding portion of the interior surface of the socket. The second sealed volume is fluidly separated from the first sealed volume. This allows the prosthetic system to separate vacuum or pressure functions. The first sealed volume can promote vacuum suspension between the liner and the socket and the second sealed volume can promote sweat or fluid removal from the inside of the liner.

This advantageously reduces the likelihood of excessive suction directly on the skin surface of the residual limb. For instance, elevated vacuum inside the liner via the second sealed volume can be maintained below a target vacuum level (e.g., about 50 mmHg). This can be important because blisters and other problems are common at vacuum levels on the skin surface beyond about 50 mmHg below atmospheric pressure. Elevated vacuum for suspension applied to the outside of a liner to secure it to a socket is commonly 250 mmHg or greater, well above comfortable or desirable vacuum levels inside of the liner. The prosthetic system can thus beneficially create or maintain a higher vacuum in the first sealed volume for suspension and a lower, more comfortable vacuum level inside the liner via the second sealed volume for fluid or sweat removal.

BRIEF DESCRIPTION OF THE DRAWINGS

These and other features, aspects, and advantages of the present disclosure will become better understood regarding the following description, appended claims, and accompanying drawings.

FIG. 1 is a cross section view of a prosthetic system according to an embodiment.

FIG. 1A is a detailed view of the liner body in FIG. 1 according to an embodiment.

FIG. 2 is a detailed cross section view of a liner body according to another embodiment.

FIG. 8 is a partial cross section view of a liner according to another embodiment.

FIG. 8A is a detailed view of the liner body in FIG. 8.

FIG. 10 is a cross section view of a locking pin according to an embodiment.

FIG. 11 is a cross section view of a locking pin according to another embodiment.

DETAILED DESCRIPTION OF VARIOUS EMBODIMENTS

Figures 3, 4, 5:
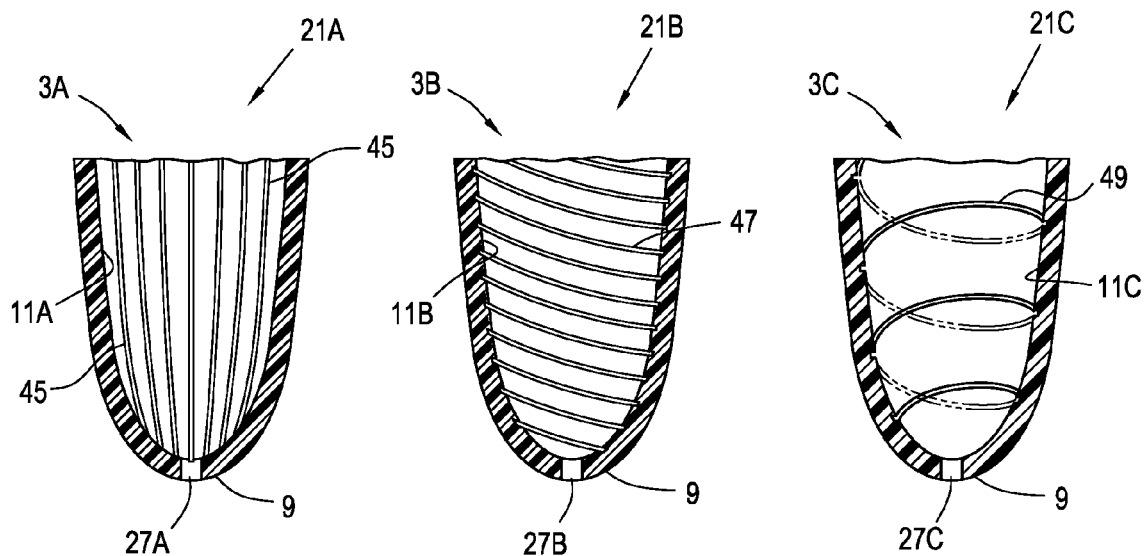
FIG. 3 is a cross section view of a liner according to another embodiment.
FIG. 4 is a cross section view of a liner according to another embodiment.
FIG. 5 is a cross section view of a liner according to another embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

For further ease of understanding the disclosure, a description of a few terms is necessary. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the prosthetic system. The term "rigid" is intended to denote that an element of the system is generally devoid of flexibility. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to connote properties of elements that provide support and are free-standing; however, such elements may have some degree of flexibility or resiliency.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function, or "step for" performing a specific function is not to be interpreted as a "means" or "step" clause as specified in 35 U.S.C. § 112, paragraph 6.

FIG. 1 shows an embodiment of the prosthetic system 1 comprising a liner 3 and a pump system 30. The liner 3 is configured to be donned on a residual limb (not shown) of an amputee. Typical liners are made of soft, stretchy material and protect the residual limb and act as an interface between a hard, weight bearing socket and the skin of the limb. The liner 3 has a liner body 5 defining a proximal end 7, which is open, and a distal end 9, which is closed. The liner body 5 defines an inner surface 11 that interfaces with the skin, and an outer surface 13 opposing the inner surface 11. The liner body 5 can be formed of a polymeric or elastomeric material like silicone, copolymer gel, polyurethane, combinations thereof, or any other suitable material.

The inner surface 11 of the liner body 5 can include one or more features arranged to both secure a residual limb within the liner 3 and promote movement of fluid away from the user's skin surface.

The inner surface 11 can include a first or proximal part 19 and a second or distal part 21. The proximal part 19 defines a first region 22 arranged for creating a seal between the proximal part 19 and the residual limb. The first region 22 can be substantially smooth, non-textured or less textured. The seal between the proximal part 19 and the residual limb is beneficial because failure of the liner 3 to seal properly against the skin proximally lets in air, which can compromise suspension and in worst case the prosthesis may fall off. Further, the seal between the proximal part 19 and the residual limb helps reduce the likelihood of air pockets, which can be very uncomfortable and can cause rubbing and movement between the liner 3 and the residual limb.

Below the proximal part 19, the inner surface 11 can include the distal part 21 defining a second region 23 arranged to promote movement of fluid and/or moisture away from the interface between the liner body 5 and the user's skin surface. The second region 23 can comprise a textured region 23. The textured region 23 can be defined or formed in the material forming the liner body 5. In other embodiments, the textured region 23 can be formed in a substrate chemically connected with the material forming the liner body. The textured region 23 can be generally homogenous or variable as described in more detail below.

As noted above, the textured region 23 can promote the movement of fluid away from the skin surface of the user. It will be appreciated that the term "fluid" may refer to any liquid or gas, including, but not limited to, water, sweat, air, water vapor, or other suitable substance. For instance, the textured region 23 on the distal part 21 of the liner body 5 can promote the movement of sweat or exudate away from the user's skin surface.

When the liner 3 is donned on a residual limb, the textured region 23 forms a plurality of spaces 25 between the distal part 21 and the skin surface. The spaces 25 can be located radially inside and/or radially outside of a profile defined by the first region 22 along the proximal part 19. The spaces 25 promote movement of fluid away from the skin by providing areas of lower pressure into which fluid can flow. When the residual limb begins to sweat, at least some of the sweat can flow away from the skin and collect in the spaces 25, providing a wicking effect.

Because the first region 22 of the proximal part 19 seals against the user's skin surface, the spaces 25 can be present on the distal part 21 without compromising the fit of the liner 3 on the residual limb. This advantageously allows the prosthetic system 1 to both positively secure the residual limb within the liner 3 and promote movement of fluid or moisture away from the user's skin surface, increasing user comfort and safety.

The textured region 23 thus beneficially provides a solution which effectively moves fluid away from the surface of the skin. Conventional methods to obtain wicking/removal function have nearly always if not solely relied on some kind of fabric to wick and contain moisture. As noted above, the textured region 23 can be defined by the material forming the liner body 5 or a substrate chemically connected with the liner body material, instead of a separate and/or mechanically infused sock next to or embedded in the liner surface. This advantageously results in a liner which is much easier to maintain, clean, and use than a multicomponent, fabric based system as in the prior art where hygiene is always an issue.

The capacity of the spaces 25 to store fluid may be limited and/or become saturated once a specific amount of fluid is contained within the spaces 25. According to a variation, the prosthetic system 1 may include one or more features arranged for emptying, draining, and/or flushing fluid from the spaces 25. For instance, one or more flow channels 26 can be formed along the textured region 23 between and/or through the spaces 25. In an embodiment, the spaces 25 can comprise the flow channels 26. At least some of the flow channels 26 are in fluid communication with the distal end 9 of the liner.

Fluid or sweat generated at the interface between the distal part 21 and the skin surface can first collect in the spaces 25 and then move into and/or through the flow channels 26, extracting the fluid or sweat away from the skin surface. Alternatively, the fluid or sweat can flow directly into the flow channels 26.

Once in the flow channels 26, the fluid or sweat can be drained or drawn through the flow channels toward the distal end 9 of the liner 3. In an embodiment, the fluid or sweat can be actively drawn through the flow channels 26 toward the distal end 9 using a pump system 30 as shown in FIG. 1. Any suitable pump system can be used. Some examples of suitable pump systems can be found in U.S. Pat. Nos. 9,044,348; 9,072,617; and 9,198,780 and U.S. patent application Ser. Nos. 14/988,503; 15/161,464; and 15/163,117, incorporated herein and commonly owned by the assignee of this disclosure. In other embodiments, the sweat can be drained using gravity, muscular action, motion of the amputee, an electrical pump system, or via any other suitable method.

To permit removal of fluid from the distal part 21 of the liner 3, an aperture or outlet 27 is defined in distal end 9 of the liner body 5. The outlet 27 extends through the inner and outer surfaces 11, 13. The inside of the liner 3 can be in fluid communication with atmosphere or an environment external to the liner 3 via the outlet 27.

Optionally, a valve may be provided separately or integrally with the outlet 27 and/or the pump system 30. The valve can be a one-way valve that selectively permits fluid to flow from the inner surface 11 of the liner body 5 to atmosphere. This beneficially reduces the likelihood of sweat undesirably pooling within the distal end of the liner 3.

To permit introduction of fluid (e.g., air) into the inside of the liner 3, one or more apertures or inlets 31 can be defined through the liner body 5. The inlets 31 can be located in any suitable location but are shown extending through the inner surface 11 and the outer surface 13 at or near the transition between the proximal part 19 and the distal part 21. The inlets 31 allow the distal part 21 of the inner surface 11 to be in fluid communication with an area external to the liner 3 (e.g., atmosphere), which, in turn, promotes the fluid flow between the distal part 21 and the skin surface toward the outlet 27.

The fluid communication between the outlet 27 and the inlets 31 can vent the inside of the liner 3 below the proximal part 19, facilitating drainage of perspiration out of the liner 3 through the outlet 27, preferably for disposal.

According to a variation, the system 1 can also help move heat away from the skin surface. For instance, the pump system 30 can actively draw air into the liner 3 through at least one of the inlets 31 and between the distal part 21 and the skin surface. The pump system 30 can be connected to the outlet 27 via a tube 28. The pump system 30 can pull the air through the spaces 25 and flow channels 26 along the inner surface 11 and out the outlet 27, providing a cooling effect and/or removing heat across the skin, which, in turn, can reduce sweating or perspiration. In other embodiments, the pump system 30 can pull sweat from the spaces 25 and through the flow channels 26 and out the outlet 27, actively extracting sweat from the liner 3.

According to a variation, one or more valves 34 may be provided separately or integrally with the one or more inlets 31. The valves 34 can be arranged to selectively permit air flow into and/or out of the liner 3 to generate or maintain a predetermined pressure differential between the inside of the liner 3 and atmospheric pressure or pressure external to the liner 3. As described in more detail below, the predetermined pressure differential can promote cooling and/or drainage of sweat inside of the liner 3 while maintaining a higher vacuum outside the liner 3 for safe and secure suspension.

The pressure differential between the inside of the liner 3 and atmosphere or a volume defined between the liner 3 and a socket can be between about 50 mmHg and about 300 mmHg, about 80 mmHg and about 280 mmHg, about 110 mmHg and about 260 mmHg, about 140 mmHg and about 240 mmHg, or about 160 mmHg and about 220 mmHg. In other embodiments, the pressure differential can be greater or smaller between the inside of the liner 3 and atmospheric pressure or the pressure in a volume between the liner 3 and a socket. In other embodiments, the pressure in the volume between the liner 3 and the socket can be greater than about 3 times, about 4 times, about 5 times, about 6 times, about 7 times, about 8 times, about 9 times, or about 10 times the pressure inside the liner 3 or along the distal part 21 of the inner surface 11.

According to a variation, the valves 34 can be arranged to operate based on a user's gait. For instance, the valves 34 can be arranged to introduce a selected dosage or volume of air into the liner 3 in swing phase. This selected dosage of air can advantageously promote cooling and/or drainage of sweat or other fluid out the outlet 27 without causing the liner 3 to fall off the residual limb. During stance, pressure inside the liner 3 can equalize and the valves 34 can reset, allowing for another selected dosage of air in the next swing phase. As such, the system 1 can efficiently cool and/or remove sweat or other fluids from the liner 3 in each step. In an embodiment, the valves 34 can be a one-way valve that selectively permits fluids to flow from outside of the liner 3 through the one or more inlets 31 to the distal part of the inner surface 11.

In other embodiments, the textured region 23 on the inner surface 11 can drain blood and/or other fluids associated with a wound site away from the wound site. Similar to sweat, such fluids may be drained using gravity, muscular action, motion of the amputee, mechanical pump systems, and/or electrical pump systems.

In other embodiments, the textured region 23 can be used to control movement of fluids toward the skin surface. For instance, the textured region 23 can facilitate the movement and/or dosing of medication to a wound site and/or the skin surface. The textured region 23 can facilitate the movement and/or dosing of silicone additives toward the skin surface. Silicone additives can include, for example, essential oils, aloe vera, petroleum products (e.g., Vaseline), or other products with benefits for the skin. The textured region 23 on the distal part thus beneficially can help keep the residual limb healthy and reduce the likelihood of wounds on the skin surface from the liner.

FIG. 1A is a partial detailed view of the textured region 23 according to an embodiment. As described above, the liner body 5 can be formed from an elastomer, such as silicone, which is generally hydrophobic. Rubbing and/or movement as a result of wet, slippery surfaces usually causes problems with prosthetic liners. The hydrophobic properties of the liner body 5 help in maintaining the position of the liner on the skin it is supporting at least in part by repelling moisture.

As seen in FIG. 1A, the textured region 23 can include the spaces 25 comprising a plurality of recessed portions 35 and smoother or generally flat portions 37 extending between and separating the recessed portions 35. The recessed portions 35 can have a generally hydrophilic configuration. For instance, the recessed portions 35 include matte surfacing to break surface tension of fluids, allowing for a wicking effect.

According to a variation, the generally flat portions 37 can have a generally hydrophobic configuration or glossy surfacing arranged to reduce contact of sweat with the smooth portions 37. This beneficially allows the recessed portions 35 to capture and wick moisture away from the skin surface while the smoother portions 37 surrounding the recessed portions 35 maintain a secure connection between the liner and the skin surface.

FIG. 2 illustrates a textured region 39 along the distal part of the liner body 5 according to another embodiment. In this embodiment, the textured region 39 includes a coarser texture portion 41 with a finer sub-texture portion 43 applied. The finer sub-textured portion 43 can be located in spaces 42 defined by the textured region 39, defining a hydrophilic surface that attracts and retains moisture in the flow channels. Similar to the previously described embodiments, the coarser texture portion 41 can define sub spaces or flow channels for extracting fluid away from the skin. The textured region 39 can thus both extract and keep moisture away from the skin surface.

As noted above, the inner surface of the liner can define flow channels for draining away from and/or towards the skin surface. The flow channels are described as being formed by texturing but may be formed in any suitable manner. The flow channels can be arranged in any suitable manner to help convey moisture to the distal end 9 of the liner body 5. The flow channels can have varying sizes, shapes, depths, inlet areas based on different factors such as comfort, moisture accumulation, high perspiration regions, and/or other factors.

FIGS. 3-8 illustrate embodiments of the liner including different flow channel configurations. For ease of reference to the flow channels, the liner body of the liner is illustrated in cross section.

FIG. 3 illustrates a liner 3A according to another embodiment having an inner surface 11A defining a plurality of flow channels 45 in a distal part 21A of the inner surface 11A. The flow channels 45 are distributed circumferentially about the liner 3A and extend generally in an axial direction along the distal part 21A. The flow channels 45 can extend completely or partially between an outlet 27A at the distal end 9 and a proximal end of the distal part 21A. In other embodiments, the flow channels 45 can be distributed about only a portion of the liner 3A.

When the liner 3A is positioned on a residual limb, the flow channels 45 define generally vertical flow paths along the inner surface 11A into which sweat or other fluids can flow toward the outlet 27A at the distal end of the liner 3A. These vertical flow paths can reduce flow time for the sweat to move through the distal part 21A of the liner 3A, which, in turn, can help reduce the likelihood of the flow channels 45 and inner surface 11A becoming saturated with sweat, improving user comfort.

FIG. 4 illustrates a liner 3B according to another embodiment having an inner surface 11B defining a plurality of flow channels 47 in a distal part 21B of the inner surface 11B. As seen, the flow channels 47 are distributed along an axis of the liner 3B and extend in obliquely to the axis. The flow channels 47 can be distributed along the entire length of the distal part 21B between an outlet 27B at the distal end 9 and a proximal end of the distal part 21B. In other embodiments, the flow channels 47 can extend along a portion of the length of the distal part 21B.

When the liner 3B is positioned on a residual limb, sweat flowing or draining downward along the inner surface 11B toward the outlet 27B must flow across and/or through one or more the flow channels 47. This beneficially promotes movement of the sweat or another fluid away from the skin surface of the user, improving the moisture management capacity of the liner 3B. In an embodiment, each flow channel 47 can be fluidly separate from another. In other embodiments, two of more of the flow channels 47 can be interconnected.

According to a variation, the volume and/or cross-sectional area of the flow channels 47 can increase in a direction toward the outlet 27B. This increase in volume can be within an individual flow channel 47 and/or from one flow channel 47 to another. This is advantageous as the total volume of sweat moving along the inner surface can increase in a direction toward the outlet 27B.

FIG. 5 illustrates a liner 3C according to another embodiment having an inner surface 11C defining a flow channel 49 on a distal part 21C of the inner surface 11C. The flow channel 49 is shown spiraling around the distal part 21C between a proximal end of the distal part 21C and an outlet 27C at the distal end 9.

When the liner 3C is positioned on a residual limb, sweat flowing along the inner surface 11C enters the flow channel 49 and is routed multiple times around the distal part 21C. Because the flow channel 49 spirals completely around the distal part 21C, sweat flowing or draining along the inner surface 11B must flow across and/or through the flow channel 49. In addition, the spiraling of the flow channel 49 multiple times around the inner surface 11B increases the length of the flow channel 49. This lengthens flow time and flow channel capacity along the inner surface 11C, promoting evaporation and movement of the sweat away from the skin surface of the user.

Figures 6, 7:
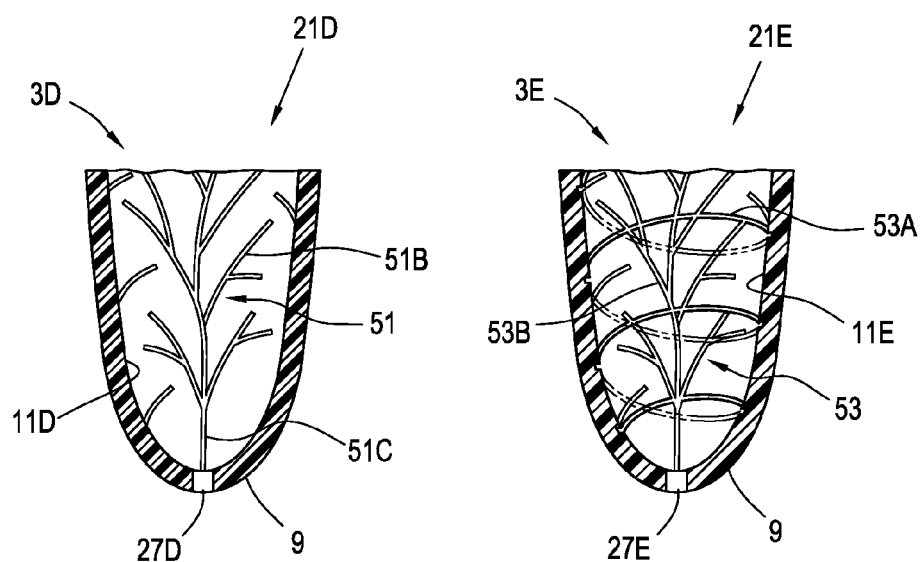
FIG. 6 is a cross section view of a liner according to another embodiment.
FIG. 7 is a cross section view of a liner according to another embodiment.

FIG. 6 illustrates a liner 3D according to another embodiment having an inner surface 11D defining a plurality of flow channels 51 in a distal part 21D of the inner surface 11D. As seen, the flow channels 51 can have a branched configuration including at least one main flow channel 51C and secondary flow channels 51B branching from the main flow channel 51C, allowing the flow channels 51 to extend in both axial and circumferential directions. The main flow channel 51C can be fluidly connected to an outlet 27D at the distal end 9 and the secondary flow channels 51B can be fluidly connected to the main flow channel 51C.

The main and secondary flow channels 51C, 51B can have varying cross-sectional areas. For instance, the main flow channel 51C can have a larger cross-sectional area than the secondary flow channels 51B extending from the main flow channel 51C, varying flow rate and/or flow velocity of sweat or other fluid flowing through the flow channels 51.

According to a variation, the flow channels 51 can be arranged to have specific flow capacities in targeted regions of the inner surface 11D. For instance, the flow channels 51 can be arranged to have a greater flow capacity where the residual limb is prone to greater perspiration, such as along the front inside or outside of the mid tibia, increasing the wicking or moisture removal effect of the liner 3D.

FIG. 7 illustrates a liner 3E according to another embodiment having an inner surface 11E defining a flow channel 53 in a distal part 21E of the inner surface 11E. The flow channel 53 can comprise a combination of spiral and branched segments. For instance, the flow channel 53 can include a main flow channel 53A that spirals around the distal part 21E and is fluidly connected to an outlet 27E in the distal end 9. A plurality of secondary flow channels 53B branch out from the main flow channel 53A. In other embodiments, the flow channels 53 can exhibit a combination of spiral, branched, vertical, oblique, and/or any other suitable combination of configurations.

FIG. 8 illustrates a liner 3F according to another embodiment having an inner surface 11F defining a plurality of flow channels 55 in a distal part 21F of the inner surface 11F. The flow channels 55 can comprise a plurality of interconnected segments 57, collectively draining toward an outlet 27F in the distal end 9. In an embodiment, at least some of the segments 57 can circumferentially extend around a portion of the inner surface 11F and arc downwardly from at least one side portion of the liner body 5 toward a central portion 58 where substantially all of the segments 57 intersect a distal adjacent one of the segments 57. The segmented and interconnected configuration of the flow channels 55 increases the overall length of the flow channel, lengthening the flow time and flow channel capacity along the inner surface 11F. As discussed above, this can promote evaporation and movement of sweat or other fluids away from the skin surface of the user.

According to a variation, at least one of the segments 57 is arranged to open and close during ambulation. As seen in FIG. 8A, at least one of the segments 57 can define a pair of undercuts 59 such that a cross section of the segment 57 tapers toward an inlet opening 61 formed in the segment 57.

When the liner body 5 is compressed between the residual limb and a socket during ambulation, the undercuts 59 of the segment 57 can collapse or fold inward toward a bottom 60 of the segment 57 opposite the inlet opening 61, causing the inlet opening 61 to close.

When the liner body 5 is decompressed between the residual limb and the socket during ambulation, the undercuts 59 can return to their original position, causing the inlet opening 61 to reopen.

The flow channel segments 57 can thus collect and convey fluid (e.g., sweat) on decompression and close and convey fluid on compression. It will be appreciated that while the segment 57 is described including undercuts tapering toward the inlet opening 61, the segment 57 can include any suitable configuration that can open and close during ambulation.

Figure 9:
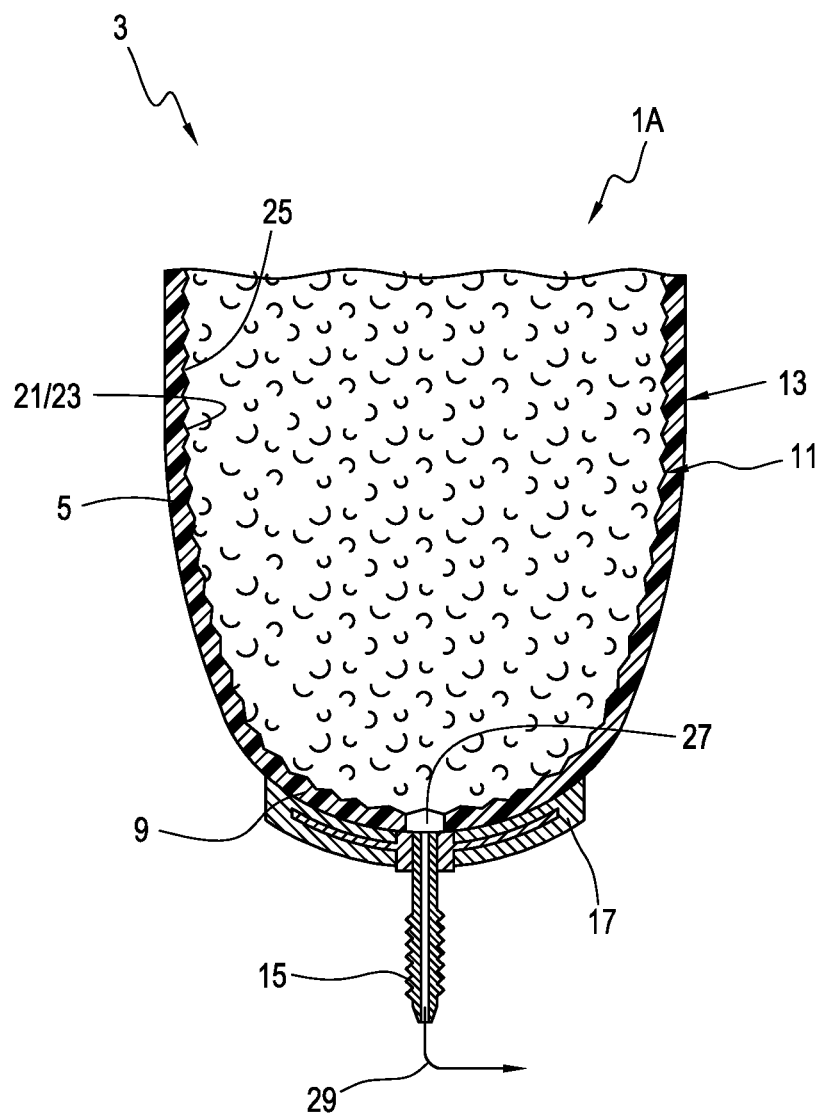
FIG. 9 is a partial cross section view of a prosthetic system according to another embodiment.

FIG. 9 illustrates another embodiment of a prosthetic system 1A. The prosthetic system 1A can be similar to the prosthetic system 1 except that a pin 15 is secured to the distal end 9 of the liner body 5. The pin 15 may be mounted to the liner 3 by being molded thereto or screwed into the distal end 9 of the liner body 5. According to a variation, the liner body 5 includes an umbrella member 17 at its distal end 9 for securing the pin 15 to the liner 3. The pin 15 is adapted to extend through an axial opening in a distal end of a socket for securing the socket relative to a prosthesis mounted to the distal end of the socket.

In the illustrated embodiment, the outlet 27 of the distal part 21 can be defined at least in part by the pin 15. For instance, the pin 15 can have a hollow configuration defining a flow channel 29 in fluid communication with the inner surface 11 and a location outside of the liner 3.

FIG. 10 illustrates another embodiment of a pin 63 defining a through channel 29. For instance, the pin 63 can have a shaft 64 defining open ended channel 65 in fluid communication with a location outside the liner, a head portion 66 defining a recess 67. The recess 67 can be in fluid communication with the channel 65 and the inner surface 11 of the liner 3, providing a flow path for fluid or moisture at the distal end 9 of the liner body 5 to drain from the liner 3.

FIG. 11 illustrates another embodiment of a pin 69 including an outer surface 68 having surface texturing 70, providing additional flow paths along the outer surface 68 for moisture at the distal end 9 of the liner body 5 to drain away from the skin surface. The surface texturing 70 is shown as a spiraling channel but may include any suitable surface feature.

Figure 12:
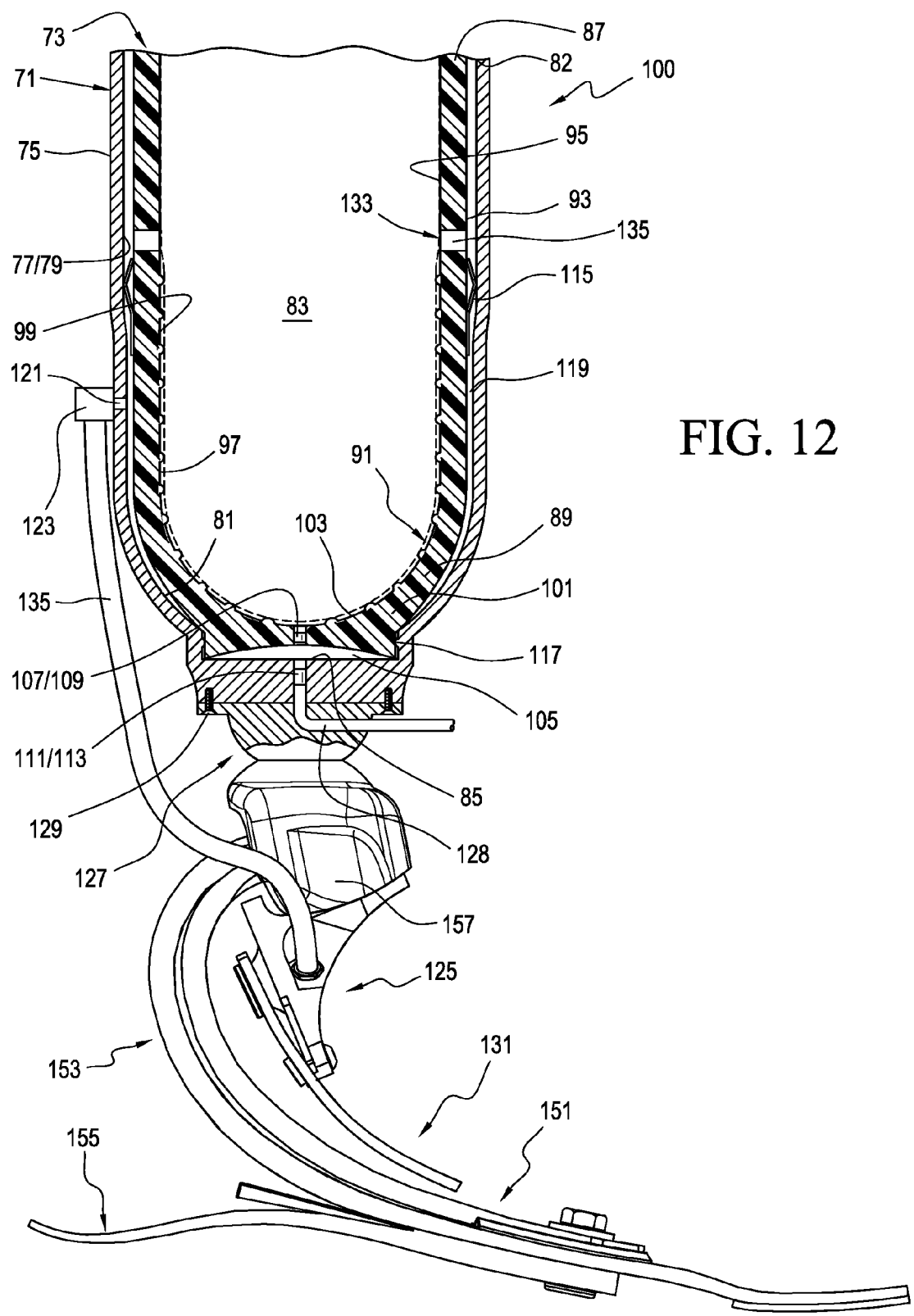
FIG. 12 is a cross section view of a prosthetic system according to another embodiment.

FIG. 12 illustrates another embodiment of a prosthetic system 100 arranged for heat and/or moisture management. The system 100 includes a pump system 125 and a prosthetic foot 131. The prosthetic system 100 has a socket 71, a liner 73, a tube 135 connecting the pump system 125 to the socket 71, and the prosthetic foot 131. The prosthetic foot 131 can comprise any suitable foot.

As discussed in more detail below, the system 100 can define one or more fluidly separate sealed volumes that allow the system 1 to separate vacuum or pressure functions. For instance, the system 100 can define a first sealed volume for vacuum suspension and a second sealed volume fluidly separate from the first sealed volume for sweat or moisture removal. In other embodiments, the system 100 can define a first sealed volume for increasing pressure between the liner 73 and the socket 71 to assist in doffing and a second sealed volume fluidly separate from the first sealed volume for sweat or moisture removal or cooling.

The socket 71 has an outer surface 75 and an opposing interior surface 77 defining a socket cavity 79. The interior surface 77 is arranged as a close-ended cup with an open proximal end 82 and a closed distal end 81. The open proximal end of the interior surface 77 is adapted to receive a distal portion of a residual limb 83 to be located in the socket cavity 79. The closed distal end 81 of the interior surface 77 includes a portion defining a receptacle 85 arranged to receive and support a distal end of the liner 73 described below. The receptacle 85 is shown having a generally cylindrical configuration but can have any suitable shape.

The liner 73 is adapted to be removably positioned within the socket cavity 79 and to receive the distal portion of the residual limb 83. The liner 73 can include a liner body 87 defining a proximal end, which is open, and a distal end 89, which is closed. The liner body 87 defines an inner surface 91 that interfaces with the skin, and an outer surface 93 opposing the inner surface 91.

Similar to the liners previously described, the inner surface 93 of the liner 73 includes one or more features to both secure the residual limb 83 within the liner 73 and to promote movement of heat and moisture away from the user's skin surface. For instance, the inner surface 93 includes a proximal part 95 and a distal part 97. The proximal part 95 defines a non-textured or less textured region arranged for creating a seal between the proximal part 95 and the residual limb 83 similar to the proximal part described above. The proximal part 95 can define a smooth region on the inner surface 91. The distal part 97 defines a textured region 99 arranged to promote movement of sweat or other fluids away from the skin surface of the user similar to the distal part described above.

According to a variation, the distal end 89 of the liner body 87 defines a pump mechanism 101. The pump mechanism 101 can be an expulsion cup dimensioned and arranged to be situated within the receptacle 85 of the socket 71. A recess 103 is defined in a bottom of the pump mechanism 101. The recess 103 may have any desired shape, but is shown having a concave shape.

A first sealed volume or a fluid chamber 105 is defined between the recess 103 of the pump mechanism 101 and a bottom of the receptacle 85. The pump mechanism 101 is movable between a compressed configuration in which the volume of the fluid chamber 105 is at a first volume, and an original configuration (shown in FIG. 12) in which the volume of the fluid chamber 105 is increased or is greater than the first volume.

To permit introduction of fluid into the fluid chamber 105 from the inside of the liner 73, an outlet or passageway 107 is defined in the liner body 87 that extends through distal part 97 of the inner surface 91 and the outer surface of the distal end 89. The fluid chamber 105 can be in fluid communication with the distal part 97 of the inner surface 91 via the passageway 107. Optionally, a valve 109 may be provided separately or integrally with the passageway 107. The valve 109 can be a one-way valve that selectively permits fluid to flow from the inner surface 91 of the liner body 87 through the passageway 107 to the fluid chamber 105.

To permit expulsion or purging of fluid (e.g., sweat and/or air) from the fluid chamber 105, an aperture or outlet 111 can be defined by the socket 71 that extends through the interior surface 77 toward the closed distal end and the outer surface 75 of the socket 71. The fluid chamber 105 can be in fluid communication with atmosphere external to the socket 71 via the outlet 111. A valve 113 may be provided separately or integrally with the outlet 111. The valve 113 can be a one-way valve that selectively permits fluid to flow from the fluid chamber 105 through the outlet 111 to atmosphere external to the socket 71, but not in the other direction.

In some embodiments, a mounting plate system 127 can be attached to a bottom of the socket 71 via one or more fasteners 129. The mounting plate system 127 can have a top face to interface with the socket 71, and a bottom face for attachment to the prosthetic foot 131 or another prosthesis. The mounting plate system 127 can define at least one channel 128 therein for fluid communication between the outlet 111 of the socket 71 and atmosphere. The mounting plate system 127 can be any suitable mounting system such as the mounting plate system described in U.S. Pat. No. 8,551,185, incorporated herein by this reference. While the valve 113 is described being associated with the outlet 111, in other embodiments, the valve 113 can be associated with the channel defined mounting plate system 127 and/or a tube in fluid communication with the outlet 111.

When a downward force is exerted on the pump mechanism 101 in a direction toward the bottom of the receptacle 85, the pump mechanism 101 moves toward the compressed configuration as the pump mechanism 101 deforms or collapses, causing a decrease in the volume of the fluid chamber 105. This decrease in volume of the fluid chamber 105 can pull sweat or another fluid from the fluid chamber 105 to atmosphere.

Once the force is removed from the pump mechanism 101, the pump mechanism 101 returns toward its original configuration as the pump mechanism 101 moves away from the bottom of the receptacle 85, causing an increase in the volume of the fluid chamber 105. This increase in volume of the fluid chamber 105 can draw fluid or sweat into the fluid chamber 105 from the inside of the liner 73 through the passageway 107. Similar to the embodiments previously described, the fluid can collect and/or flow through flow channels defined in the textured region 99 along the inner surface 91. The pump mechanism 101 can be elastomeric and can use at least in part its material properties to naturally or elastically return to its original position away from the bottom of the receptacle 85.

According to a variation, the pump mechanism 101 is arranged to create a maximum vacuum level or negative pressure of less than about 75 mmHg inside the liner 73. The pump mechanism 101 can create a vacuum level between about 30 mmHg and about 50 mmHg. This is beneficial as elevated vacuum applied directly to the skin can be risky and prone to create blisters and problems if the vacuum level is greater than about 50 mmHg below atmospheric pressure. In other embodiments, the pump mechanism 101 is arranged to generate a vacuum level inside the liner 73 between about 20 mmHg and about 60 mmHg or between about 35 mmHg and about 55 mmHg. In other embodiments, the pump mechanism 101 is arranged to generate a higher or lower vacuum level inside the liner 73.

At least one passageway or vent inlet 133 can be defined in the liner body 87. According to a variation, the at least one vent inlet 133 includes a valve assembly 135 arranged to selectively permit air flow into the liner 3 until a selected pressure differential is reached between the inside of the liner 73 and a sealed volume between the liner 3 and the socket 71. This helps ensure that the liner 73 does not fall off the socket 71, while allowing the pump mechanism 101 to vent the inside of the liner 73 as soon as the prosthetic system 101 is capable of doing so.

According to a variation, the prosthetic system 100 can use the motion of the amputee to extract sweat or other fluids from the inside of the liner 73. For instance, when the user puts his weight on the liner 73 and/or the prosthetic foot 131 such as upon heel strike, mid-stance, and/or toe-off, the user's weight can cause the pump mechanism 101 to move toward the compressed configuration, expelling fluid or sweat from the fluid chamber 105 to atmosphere. After the weight is removed, and/or shifted, the pump mechanism 101 can return toward its original configuration, drawing fluid or sweat into the fluid chamber 105 from the inside of the liner 73 through the passageway 107.

Because the pump mechanism 101 operates on motion of the amputee, it can remove more sweat when the user is participating in a higher activity event such as running, skiing, or hiking, increasing efficiency of the prosthetic system 100. Further, because the pump mechanism 101 includes few moving parts and no electric function or batteries, the prosthetic system 100 is simpler than the prior art and the likelihood of the pump mechanism 101 malfunctioning or failing is reduced.

The prosthetic system 100 can define a second sealed volume between the liner 73 and the socket 71. As noted above, the second sealed volume can be fluidly separate from the first sealed volume or the fluid chamber 105. For instance, the prosthetic system 100 can include a vacuum suspension system having a first seal element 115 associated with the liner 73 or the socket 71 to create a first seal between the socket 71 and the liner 73. A seal may refer to a component of the prosthetic system 100 that allows a vacuum to be formed between the socket 71 and the liner 73. The first seal element 115 can be located proximally of the receptacle 85. The first seal element 115 can be located between the proximal and distal ends of the liner 73. The first seal element 115 can be located about halfway between the proximal and distal ends of the liner 73. The first seal component 115 can be a hypobaric seal, membrane, or any other suitable seal component. Other examples of suitable seal elements are found in U.S. Pat. Nos. 8,308,817; 8,097,043; 8,052,760; 8,034,120; 8,372,159; 8,372,159; 8,894,719; 8,956,422; 8,911,506; 9,056,022; 9,072,611; 9,060,885; 9,066,821, and U.S. patent application Ser. Nos. 13/826,748; and 14/281,424, each of which are incorporated herein by reference in their entirety.

A second seal element 117 can be disposed below or distal of the first seal element 115 and associated with the liner 73 or socket 71 to create a second seal between the socket 71 and the liner 73. The second seal element 117 can be located near or within the receptacle 85 as seen. Like the first seal element 115, the second seal element 115 can be any suitable seal element.

A second sealed volume or a substantially sealed volume 119 is defined between the first and second seal elements 115, 117, and between at least a portion of the outer surface 93 of the liner body 87 and a corresponding portion of the interior surface 77 of the socket 71, substantially isolating this area from atmosphere and the fluid chamber 105.

To permit expulsion of fluid (e.g., air) from the substantially sealed volume 119, an aperture 121 can be defined by the socket 71 that extends through the interior surface 77 and the outer surface 75 of the socket 71. The substantially sealed volume 119 can be in fluid communication with atmosphere external to the socket 71 via the aperture 121. A valve 123 may be provided separately or integrally with the aperture 121. The valve 123 can be a one-way valve that selectively permits fluids to flow from the substantially sealed volume 119 through the aperture 121 to atmosphere external to socket 71, but not in the other direction.

According to a variation, the pump system 125 or other device may be in fluid communication with the substantially sealed volume 119 via the tube 135 connected to the aperture 121. The pump system 125 can create an elevated vacuum environment in the substantially sealed volume 119, improving suspension. Similar to the previously described embodiments, the pump system 125 can be any suitable type of pump such as a membrane type pump. Other examples of the pump system are described in U.S. patent application Ser. Nos. 13/873,394; 13/873,315; 13/766,086; 62/101,154; and 62/151,518, and commercially available as the Unity Vacuum System by Össur hf. This disclosure is incorporated by reference and belongs to the assignee of this disclosure.

As seen, the pump system 125 can be operatively coupled to the prosthetic foot 131. In the illustrated embodiment, the prosthetic foot 131 can include an upper foot member 151 and a lower foot member 153, which is generally disposed below the upper foot member 151. A heel member 155 is disposed below at least a portion of the lower foot member 153. An adaptor 157 can be coupled to the upper foot member 151 and the lower foot member 153. The pump system 125 can be coupled to the prosthetic foot 131 in any suitable manner but is shown coupled to the adaptor 157. It will be appreciated that the prosthetic foot 131 can comprise any suitable prosthetic foot.

In use, the prosthetic foot 131 can expand and compress through flexion of the foot members 151, 153. The prosthetic foot 131 is in expansion when the end portions of the foot members 151, 153 are moved of flexed apart from a resting position of the foot 131, increasing the distance between the end portions. The prosthetic foot 131 is in compression when the end portions of the foot members 151, 153 are moved or flexed toward one another from the resting position of the foot, reducing the distance between the end portions of the foot members 151, 153.

In order to better understand the operation of the prosthetic foot 131, a basic discussion of the gait cycle is required. The gait cycle defines the movement of the leg between successive heel contacts of the same foot. The gait cycle has two phases: stance and swing. The stance phase generally includes heel-strike or initial contact, mid-stance, and toe-off.

It is during the stance phase that the mechanics of a prosthetic foot 131 come into play. Upon heel strike, the prosthetic foot 131 is in expansion, providing cushioning to the user. During mid-stance, at which time the weight of the user is transmitted through the prosthetic foot 131 to a supporting surface, the prosthetic foot 131 moves from expansion into compression. The prosthetic foot 131 remains in compression through toe-off until the weight of the user is removed from the prosthetic foot, at which time the prosthetic foot 131 returns to its resting position.

The pump system 125 can generate a vacuum in the substantially sealed volume 119 during compression and/or expansion of the prosthetic foot 131. For instance, upon mid-stance and/or toe-off, the prosthetic foot 131 moves into compression. In compression, the pump system 125 can move into an expanded configuration, increasing the volume of a fluid chamber defined by the pump system 125 to create a vacuum in the pump system 125, pulling fluid or air into the pump system 125 from the substantially sealed volume 119. This can help improve suspension between the liner 73 and the socket 71.

At the end of the stance phase or when the weight of the user is removed from the prosthetic foot 131, the prosthetic foot 131 returns to its resting position and the pump system 125 can return toward an original configuration, decreasing the volume of the fluid chamber to zero or near zero volume. During the return of the pump system 125 toward its original configuration, the pump system 125 expels fluid in the fluid chamber to atmosphere.

The substantially sealed volume 119 and the fluid chamber 105 of the pump mechanism 101 are fluidly separate from one another such that fluid does not flow between the substantially sealed volume 119 and the fluid chamber 105. As such, the vacuum function of the system 1 for suspension can be separated from the vacuum function of the system 1 for sweat or moisture removal. The system 1 can thus generate different vacuum pressure levels inside and outside of the liner 73. For instance, a first vacuum level can be created inside of the fluid chamber 105 to remove fluid or sweat from inside the liner 73, and a second vacuum level can be created inside of the substantially sealed volume 119 to keep the liner and socket in place on the residual limb.

This advantageously reduces the likelihood of excessive suction directly on the skin. For instance, the elevated vacuum inside the liner created by the pump mechanism 101 can be maintained below a target vacuum level (e.g., about 30 mmHg or about 50 mmHg). This is important because blisters and other problems are common at vacuum levels on the skin beyond about 50 mmHg below atmospheric pressure. Temporary suction of up to 125 mmHg is used for vacuum treatment of wounds, but with a flexible film application and for a limited time. Elevated vacuum for suspension, applied to the outside of a prosthetic liner to secure it to a socket is commonly 250 mmHg or greater, well above comfortable or desirable vacuum levels inside the liner. The system 1 can thus beneficially create or maintain a higher vacuum between the socket 71 and liner for suspension and a lower, more comfortable vacuum level inside the liner for fluid or sweat removal.

Alternatively, a pressure-throttled intake can be located proximally on the liner 73 to permit the introduction of air into the liner 73, which can be drawn out down below by the lower pressure in the pump mechanism 101. This can help in providing a cooling effect by moving air between the distal part of the liner 73 and the residual limb 83.

It will be appreciated that the embodiments described herein are to be regarded as exemplary only, as any prosthetic system is possible. For instance, while the pump mechanism is described as an expulsion cup, in other embodiments, the pump mechanism can include a membrane-type pump, a bladder-type pump, a mechanical pump, an electrical pump, or any other suitable type of pump mechanism.

In other embodiments, the liner can include a pump mechanism for removing moisture from the inside of the liner without an elevated vacuum feature for suspension. For instance, the system 100 can omit the pump system 125 and the valve 123 can be an expulsion valve that expels fluid from the substantially sealed volume as the liner 73 is inserted in the socket 71. In yet other embodiment, the pump mechanism can be defined at least in part by a locking-type liner similar to the liner shown in FIG. 1 without a second sealed volume for suspension.

In yet other embodiments, the second sealed volume 119 can selectively allow for the introduction of fluid (e.g., air) between the liner 73 and the socket 71, and/or the inside of the liner 73 and the skin. For instance, the valve 123 can be arranged to allow air to be selectively introduced or pulled into the second sealed volume 119, facilitating doffing of the liner 73 from the socket 71. In other embodiments, the liner body 87 can define apertures or flow channels that extend through the distal part 97 between the inner and outer surfaces of the liner body. This can allow air to flow from the second sealed volume 119 through the liner body 87 to the inside of the liner 73 below the proximal part 95. Once inside the liner 73, the air can flow out of the passageway 107, advantageously forcing or carrying moisture out from inside the liner 73 and/or providing a removing heat as the air moves over the textured surface 99 between the liner 73 and the skin surface.

In addition, while the liner is described defining the pump mechanism at least in part, in other embodiments, the pump mechanism may be separate from the liner. For instance, embodiments of the prosthetic system can include a pump mechanism fluidly connected to the outlet via a tube. The pump mechanism can be carried on the socket, a prosthetic foot, and/or located in any other suitable location. In other embodiments, the pump mechanism can be defined by the socket and/or a mounting plate system.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:
1. A prosthetic system comprising:
 a liner adapted to receive a residual limb therein, the liner having a liner body formed from an elastomeric material, the liner body defining:
  an open proximal end;
  a distal end;
  an outer surface;
  an inner surface opposite the outer surface and including a first part arranged to form a seal between the liner and the residual limb, and a second part having at least one flow channel arranged for promoting movement of fluid away from a skin surface of the residual limb at least one inlet in the second part and extending between the inner and outer surfaces, the at least one inlet being in fluid communication with the at least one flow channel and an area external to the liner; and
  an outlet defined in the distal end and extending between the inner and outer surfaces, wherein the at least one flow channel is defined in the elastomeric material forming the liner body and is in fluid communication with the outlet;
 a socket including an interior surface defining a socket cavity and including an outlet extending from the interior surface to an external atmosphere;
 a first sealed volume defined between a first portion of the outer surface of the liner and a first portion of the interior surface of the socket;

a second sealed volume defined between a second portion of the outer surface of the liner and a second portion of the interior surface of the socket, wherein the first sealed volume is fluidly connected to the outlet, fluidly separated from the second sealed volume by a seal element, and is independent from the second sealed volume throughout use of the system; and a valve attached to the outlet, the valve arranged to selectively control fluid flow between the inner surface of the liner and the first sealed volume.

2. The system of claim 1, wherein the first sealed volume is variable to create a first elevated vacuum between the liner and the residual limb for removing fluid from the inner surface of the liner through the outlet.

3. The system of claim 2, wherein the socket defines an aperture in an area of the second sealed volume and further comprising a pump system operatively connected to the second sealed volume via the aperture, the pump system arranged to selectively create a second elevated vacuum in the second sealed volume for securing the socket on the liner.

4. The system of claim 3, wherein the first elevated vacuum is less than the second elevated vacuum.

5. The system of claim 4, wherein a pressure differential between the first elevated vacuum and the second elevated vacuum is greater than about 200 mmHg.

6. The system of claim 3, wherein the first elevated vacuum is less than about 50 mmHg and the second elevated vacuum is greater than about 250 mmHg.

7. The system of claim 1, wherein the second part comprises a distal part defining a textured region in the elastomeric material forming the liner body.

8. The system of claim 7, wherein the textured region defines a hydrophilic surface that attracts moisture away from the skin surface.

9. The system of claim 1, wherein the at least one flow channel comprises a plurality of flow channels extending in both an axial direction and a circumferential direction.

10. A prosthetic system comprising:
a socket including an interior surface defining a socket cavity and including an outlet extending from the interior surface to an external atmosphere;
a liner adapted to receive a residual limb therein and to be removably positioned within the socket cavity, the liner including:
a liner body formed from an elastomeric material, defining an open proximal end and, a distal end, an outer surface, an inner surface opposing the outer surface and arranged to interface with a skin surface, the inner surface defining a proximal part arranged for creating a seal between the proximal part and the residual limb, and a distal part comprising a textured region arranged to move fluid away from the skin surface, the textured region formed from a same material as the liner body;
an outlet defined in the distal end; and
one or more inlets defined below the proximal part in fluid communication with the outlet via at least one flow channel, and arranged to selectively introduce air into the distal part;
a first sealed volume defined between a first portion of the outer surface of the liner and a first portion of the interior surface of the socket
a second sealed volume defined between a second portion of the outer surface of the liner and a second portion of the interior surface of the socket, wherein the first sealed volume is fluidly connected to the outlet, fluidly separated from the second sealed volume by a seal element, and is independent from the second sealed volume throughout use of the system; and
a valve attached to the outlet and arranged to selectively provide fluid communication between the inner surface of the liner and the first sealed volume.

11. The system of claim 10, wherein the first sealed volume is variable to create a first elevated vacuum between the liner and the residual limb for removing fluid from the inner surface of the liner through the outlet.

12. The system of claim 11, wherein the socket defines an aperture in an area of the second sealed volume and further comprising a pump system operatively connected to the second sealed volume via the aperture, the pump system arranged to selectively create a second elevated vacuum in the second sealed volume for securing the socket on the liner.

13. A prosthetic system comprising:
a socket including an interior surface defining a socket cavity and including an outlet extending from the interior surface to an external atmosphere;
a liner adapted to receive a residual limb therein and to be removably positioned within the socket cavity, the liner having an outer surface, an inner surface, one or more inlets arranged to selectively introduce air into a distal part of the inner surface, and at least one flow channel in fluid communication with the inlet;
a first sealed volume defined between a first portion of the outer surface of the liner and a first portion of the interior surface of the socket;
a second sealed volume defined between a second portion of the outer surface of the liner and a second portion of the interior surface of the socket, the second sealed volume being fluidly independent from the first sealed volume throughout use of the system due to a seal element provided between the first sealed volume and the second sealed volume;
an outlet defined in a distal end of the liner, in fluid communication with the one or more inlets and the at least one flow channel, and including a valve arranged to selectively provide fluid communication between the inner surface of the liner and the first sealed volume, wherein the first sealed volume is variable to create a first elevated vacuum between the liner and the residual limb for removing fluid or sweat from the inner surface of the liner through the outlet; and
a pump system operatively connected to the second sealed volume via an aperture in the socket in an area of the second sealed volume and arranged to create a second elevated vacuum in the second sealed volume for securing the socket on the liner, the second elevated vacuum being different than the first elevated vacuum.

14. The system of claim 13, wherein the liner formed from an elastomeric material and the inner surface of the liner defines a proximal part arranged for creating a seal between the proximal part and the residual limb, and the distal part comprising a textured region arranged to move fluid away from a skin surface, the textured region formed from a same material as the liner.

* * * * *